United States Patent [19]

Berger

[11] 4,341,914
[45] Jul. 27, 1982

[54] TRANSALKYLATION PROCESS WITH RECYCLE OF $C_{10}$ HYDROCARBONS

[75] Inventor: Charles V. Berger, Western Springs, Ill.

[73] Assignee: UOP Inc., Des Plaines, Ill.

[21] Appl. No.: 219,001

[22] Filed: Dec. 22, 1980

[51] Int. Cl.³ ............................................... C07C 5/22
[52] U.S. Cl. .................................................... 585/474
[58] Field of Search ......................................... 585/474

[56] References Cited

U.S. PATENT DOCUMENTS

| | | | |
|---|---|---|---|
| 2,795,629 | 6/1957 | Boedeker | 585/321 |
| 3,211,798 | 10/1965 | Burk, Jr. et al. | 585/321 |
| 3,428,701 | 2/1969 | Ward | 585/474 |
| 3,551,510 | 12/1970 | Pollitzer et al. | 585/323 |
| 3,701,813 | 10/1972 | Stenmark | 585/315 |
| 3,720,726 | 3/1973 | Mitsche et al. | 585/475 |
| 3,729,521 | 4/1973 | Gutberlet et al. | 585/475 |
| 3,780,122 | 12/1973 | Pollitzer | 585/474 |
| 3,825,613 | 7/1974 | Kmecak et al. | 585/321 |
| 3,849,340 | 11/1974 | Pollitzer | 252/455 Z |
| 3,996,305 | 12/1976 | Berger | 585/474 |
| 4,041,091 | 8/1977 | Henry | 585/470 |
| 4,083,886 | 4/1978 | Michalko | 585/475 |
| 4,101,597 | 7/1978 | Breckenridge | 585/474 |
| 4,172,813 | 10/1979 | Feinstein et al. | 585/475 |
| 4,211,886 | 7/1980 | Tabak et al. | 585/321 |

Primary Examiner—Curtis R. Davis
Attorney, Agent, or Firm—James R. Hoatson, Jr.; John F. Spears, Jr.; William H. Page, II

[57] ABSTRACT

A transalkylation process useful in producing $C_8$ alkylaromatic hydrocarbons from $C_9$ alkylaromatic hydrocarbons or a mixture of $C_7$ and $C_9$ alkylaromatic hydrocarbons. The effluent of a transalkylation zone is passed into a fractionation zone and is therein preferably separated into a light recycle stream comprising benzene and toluene and a heavy recycle stream comprising $C_9$ and $C_{10}$ alkylaromatic hydrocarbons, with both recycle streams being returned into the transalkylation zone. The recycling of $C_{10}$ hydrocarbons to the transalkylation zone increases the yield of $C_8$ alkylaromatic hydrocarbons from the transalkylation process. The transalkylation step is preferably integrated with a paraxylene separation zone and a xylene isomerization zone operated as a continuous loop receiving mixed xylenes from the transalkylation zone feed and effluent fractionation zones.

9 Claims, 1 Drawing Figure

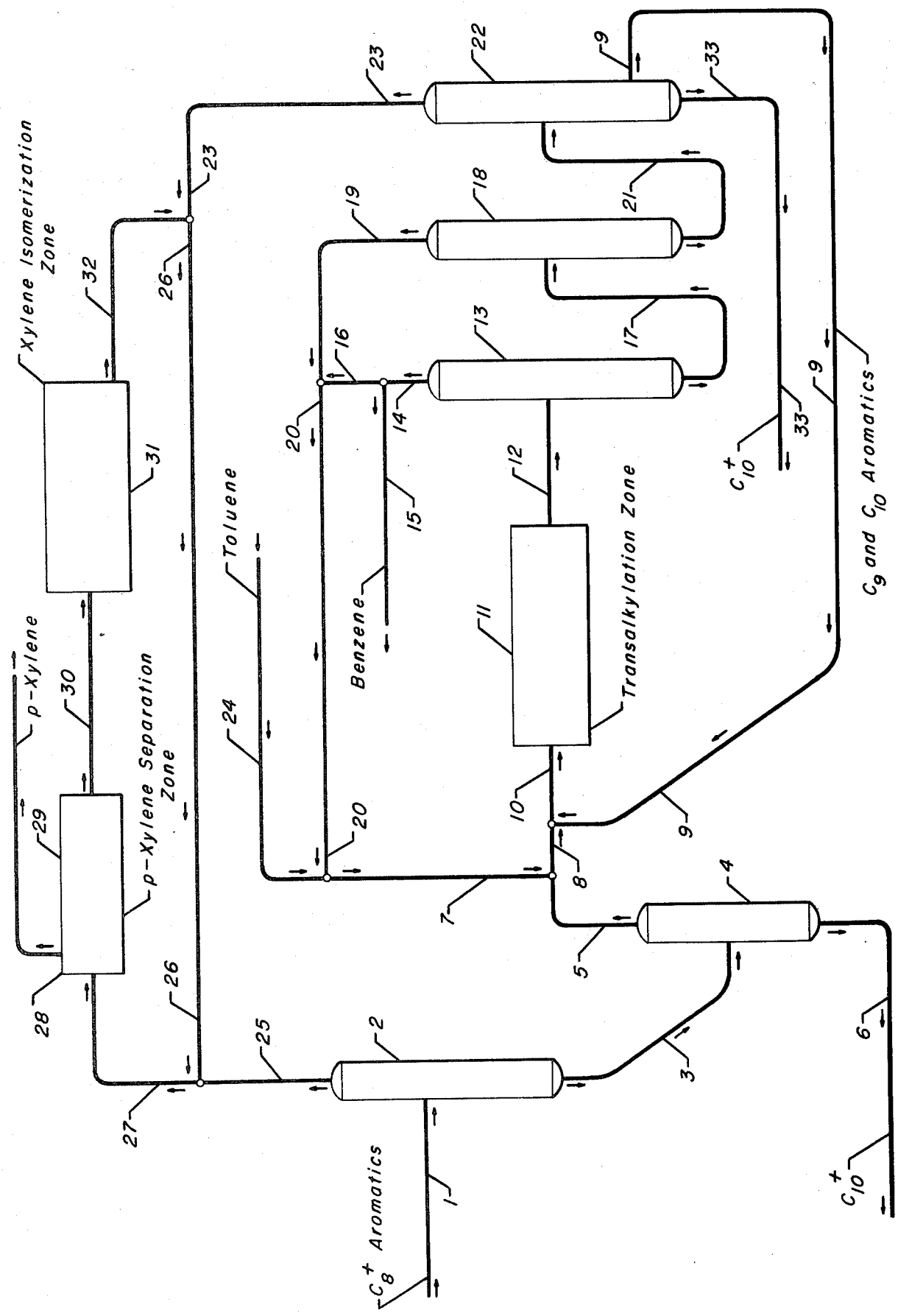

TRANSALKYLATION PROCESS WITH RECYCLE OF $C_{10}$ HYDROCARBONS

FIELD OF THE INVENTION

The invention relates to a hydrocarbon conversion process in which $C_8$ alkylaromatic hydrocarbons are produced from $C_9$ or $C_7$ and $C_9$ alkylaromatic hydrocarbons. The invention also relates to a process for producing paraxylene which employs a paraxylene separation zone and a xylene isomerization zone in series flow. The invention more specifically relates to a transalkylation process which receives a feed stream rich in $C_9$ alkylaromatic hydrocarbons and which fractionates the effluent of the transalkylation zone to produce a recycle stream comprising a mixture of $C_9$ and $C_{10}$ alkylaromatic hydrocarbons. Transalkylation is often referred to in the literature as disproportionation.

PRIOR ART

The transalkylation of alkylaromatic hydrocarbons including toluene is now practiced commercially on a large scale. Transalkylation processes are described in U.S. Pat. Nos. 2,795,629 (Cl. 260-668); 3,551,510 (Cl. 260-672); 3,701,813 (Cl. 260-668A); and 3,729,521 (Cl. 260-672T). These references exemplify catalysts, flow schemes and reaction zone conditions.

Catalysts for use in transalkylation processes are also presented in U.S. Pat. Nos. 3,720,726 (Cl. 260-672T); 3,780,122 (Cl. 260-672T) and 3,849,340 (Cl. 252-455Z). A transalkylation catalyst comprising the preferred ammonia-washed mordenite-containing base is described in U.S. Pat. No. 4,083,886 (Cl. 260-672T) issued to E. Michalko.

U.S. Pat. No. 3,996,305 (Cl. 260-672T) is pertinent for its showing of the passage of $C_9$ alkylaromatic hydrocarbons into a transalkylation zone followed by the fractionation of the transalkylation zone effluent stream into a $C_8$ product stream and a single recycle stream comprising both toluene and $C_9$ alkylaromatic hydrocarbons. U.S. Pat. No. 4,172,813 (Cl. 585-475) also shows a process for transalkylating $C_9$ alkylaromatic hyrocarbons. In this reference $C_{10}$ or $C_{10}$-plus alkylaromatics are first fractionated from a heavy reformate, which is then passed through the reaction zone in admixture with toluene and $C_9$ alkylaromatic hydrocarbons recycled from a downstream fractionation zone.

The linkage of a transalkylation zone with a paraxylene recovery zone and a xylene isomerization zone is shown in U.S. Pat. Nos. 3,211,798; 3,825,613 and 4,041,091.

U.S. Pat. No. 4,041,091 is also pertinent for its showing of the passage of some $C_9$ and $C_{10}$ alkylbenzenes into the transalkylation zone after these hydrocarbons are separated from the transalkylation zone effluent stream.

U.S. Pat. No. 4,211,886 (Cl. 585-321) describes a process for the production of benzene, toluene and xylene from a naphtha. $C_9$-plus aromatics and toluene are recycled to a heavy aromatics reactor operated at dealkylation/transalkylation conditions. The effluent of this reactor is passed into a fractionation zone having three columns. Differences between the process of this reference and various embodiments of the subject process include the fractionation method and arrangement employed, the recycling of benzene, and the method and flow of the paraxylene recovery system.

SUMMARY OF THE INVENTION

The invention provides a process for the production of $C_8$ alkylaromatic hydrocarbons from $C_9$ alkylaromatic hydrocarbons. One broad embodiment of the invention may be characterized as a transalkylation process which comprises the steps of passing a feed stream which comprises $C_9$ alkylaromatic hydrocarbons, a first recycle stream comprising toluene, and a hereinafter characterized second recycle stream which comprises a mixture of $C_9$ and $C_{10}$ alkylaromatic hydrocarbons into a transalkylation zone and thereby producing a transalkylation zone effluent stream comprising $C_6$-$C_{10}$ alkylaromatic hydrocarbons; and fractionating the transalkylation zone effluent stream in a three column fractionation zone into the second recycle stream comprising toluene, a product stream comprising benzene, a product stream comprising $C_8$ alkylaromatic hydrocarbons, a bottoms product stream comprising $C_{10}$ alkylaromatic hydrocarbons, and the second recycle stream comprising a mixture of $C_9$ and $C_{10}$ alkylaromatic hydrocarbons.

In a more limited embodiment of the invention, substantially all of the benzene and toluene present in the transalkylation zone effluent stream is concentrated into a light hydrocarbon stream which is recycled to said transalkylation zone. Furthermore, the recycle stream which contains $C_9$ and $C_{10}$ alkylaromatic hydrocarbons is removed as a sidecut stream from a product fractionator in which a bottoms product stream comprising $C_{10}$ alkylaromatics is rejected. The subject process increases the production of $C_8$ hydrocarbons through the recycling of $C_{10}$ and $C_6$ aromatic hydrocarbons. The subject invention also reduces the complexity of the fractionation zone normally associated with the recovery of a high purity $C_8$ stream and recycle streams from the transalkylation zone effluent stream. This reduces the capital costs and the utility costs of the process.

BRIEF DESCRIPTION OF THE DRAWING

The Drawing is a simplified flow diagram showing several different embodiments of the subject invention. $C_8$ alkylaromatics are removed from the $C_8$-plus first feed stream of line 1 and sent to a paraxylene recovery and xylene separation loop through line 25. After the rejection of most indane and $C_{10}$ hydrocarbons through line 6 the remaining $C_9$-plus alkylaromatics are passed into a transalkylation zone 11 in admixture with a recycle stream from line 9 which comprises $C_9$ and $C_{10}$ alkylaromatic hydrocarbons. In one optional variation of the basic process recycled benzene and toluene from line 20 and a second feed stream comprising toluene are also passed into the transalkylation zone through line 7. The transalkylation zone effluent stream is preferably separated in a three column fractionation zone into light and heavy recycle streams and a second $C_8$ alkylaromatic stream carried to the xylene separation and isomerization loop through line 23. The heavy recycle stream is removed from column 22 as a sidecut stream which may contain 50 mole percent of the $C_{10}$ alkylaromatics present in the transalkylation zone effluent stream.

DETAILED DESCRIPTION

Toluene and $C_9$ alkylaromatic hydrocarbons are presently produced at a much greater rate than is required to satisfy the demand for these hydrocarbons as reactants or products. There is, however, relatively strong and increasing demand for various xylenes, especially paraxylene. The xylenes are also very valuable as the feedstocks for many widely used petrochemicals and plastics. For instance, orthoxylene is used in the production of phthalic anhydride and paraxylene is used for the manufacture of polyesters.

Various commercial processes have therefore been developed which convert toluene and $C_9$ alkylaromatics into xylenes. These processes involve such molecular rearrangements as the transfer of the methyl groups of toluene to form benzene and xylenes and the transfer of the methyl groups of toluene and trimethylbenzenes to produce xylenes. Other $C_9$ aromatics may undergo other types of reactions. For example, ethyl groups may be transalkylated or dealkylated, while propyl groups are generally dealkylated. Since commercial $C_9$ aromatic streams include compounds of these types, it is apparent that products other than polymethyl benzenes will result. These processes are sometimes referred to as disproportionation processes, but are referred to herein as transalkylation processes.

The economic viability of any catalytic transalkylation process is dependent on several factors. One of the most important of these is the total yield of the desired product. Other important factors are the amount of by-products, the selectivity of the catalyst and the useful life of the catalyst. It is an objective of the subject invention to provide a transalkylation process providing a high yield of xylenes. It is a specific objective of the subject invention to provide a transalkylation process which yields low amounts of aromatic by-products and an increased amount of $C_8$ alkylaromatic hydrocarbons.

A specific $C_9$ aromatic which is undesirable in the present process, because it depresses catalyst activity, is indane. In typical commercial processes this compound, which is normally present at a low level less than 5%, is largely rejected by fractionation from the fresh $C_9$ aromatic feed, along with most of the $C_{10}$ aromatics. I have found, however, that very little indane survives that transalkylation reaction conditions, so that recycle of $C_9$ and higher aromatics to the reaction zone, from the products alone, does not effect catalyst activity. The independent control of heavy aromatics (and indane) derived from fresh feed and from product soures is a major part of this invention. By recycling some relatively indane-free $C_{10}$ alkylaromatics to the transalkylation zone the overall $C_8$ yield, and thus the performance, of the process is improved.

The principal fresh feed stream to the subject process is preferably a stream which is rich in $C_8$ and $C_9$ aromatic hydrocarbons. The aromatic hydrocarbons present in the feed stream may be derived from several sources and could be produced synthetically for example, by the catalytic reforming or by pyrolysis of naphtha followed by hydrotreating. A preferred source of the aromatic hydrocarbons is by extraction of aromatic hydrocarbons from a mixture of aromatic and nonaromatic hydrocarbons. For instance, high purity aromatic hydrocarbons may be recovered from a naphtha reformate through the use of a selective solvent, such as one of the sulfolane type, in a liquid-liquid extraction zone. Large quantities of aromatic hydrocarbons are recovered in this way commercially. The recovered aromatic hydrocarbons may then be separated into streams having the desired carbon number range by fractionation. However, when the severity of reforming or pyrolysis is sufficient, extraction is unnecessary, and mere fractionation is adequate.

From whatever source, a stream which is rich in $C_8$-plus aromatic hydrocarbons is passed into the first of a series of fractionation columns referred to herein as a first fractionation zone. This stream is the primary feed stream to the overall process, and preferably contains less than 5 mole percent hydrocarbons having seven or less carbon atoms per molecule. The xylenes are separated from the stream to yield a stream of $C_9$ and heavier aromatic hydrocarbons which is passed into a second column. This column produces a bottoms stream which normally contains most of the $C_{10}$ or heavier hydrocarbons charged to the column. As used herein, the term "most" is intended to indicate over 50 mole percent of the specified chemical compounds or group of compounds in the relevant process stream has been acted upon in the indicated manner. When the indane content is high in the fresh feed, more than 50 mole percent and perhaps substantially all of the $C_{10}$ and heavier aromatics are rejected in this manner.

As used herein, the term "substantially all" is intended to indicate an amount over 90 mole percent, preferably over 95 mole percent, of the total compound or grouping of compounds referred to in the context of this term's usage. In a similar manner, the term "rich" is intended to indicate a concentration over 50, preferably 65, mole percent of the indicated compound or class of compounds.

A second transalkylation zone fresh feed stream rich in toluene may be charged to the transalkylation zone. It is preferred but not necessary for the successful operation of the process that this second feed stream is charged to the transalkylation zone. The toluene present in this stream may be derived from the same sources as the other transalkylation zone fresh feed stream and may be supplemented by other available toluene. The second transalkylation zone feed stream should contain less than 10 mole percent nonaromatic hydrocarbons and less than 5 mole percent of hydrocarbons having other than seven carbon atoms per molecule. The second transalkylation zone fresh feed stream is preferably admixed with the principal transalkylation zone feed stream and the recycle stream(s) and passed into the transalkylation zone.

Sufficient hydrogen is admixed with the hydrocarbons which are passed into the transalkylation zone to form an admixture having a hydrogen to total hydrocarbon mole ratio above 2:1 and preferably above 5:1. The hydrogen to hydrocarbon mole ratio need not exceed 10:1 for successful operation of the process. This admixture is circulated through a bed of solid transalkylation catalyst located within a reaction zone as a vapor stream at an elevated temperature. The conversion which may be achieved within the reaction zone is limited by the thermodynamic equilibrium of the hydrocarbons which are present. For this reason, it is desired that the admixture contains only a small amount of any product hydrocarbon. Preferably, the feed stream contains less than 2 mole percent of any product hydrocarbon. Operating in the preferred manner normally allows a 35 to 40 mole percent conversion of the feed hydrocarbons to the product hydrocarbons.

Typically, the admixture charged to the reaction zone is first heated by indirect heat exchange against the effluent of the reaction zone and is then further heated in a fired heater. The vaporous stream is then passed through the reaction zone, which may comprise one or more individual reactors. The use of a single reaction vessel having a fixed cylindrical bed of catalyst is preferred, but other reactor configurations utilizing moving beds of catalyst or radial-flow reactors may be employed if desired. Passage of the feed admixture through the reaction zone effects the production of a vaporous effluent stream comprising hydrogen and both the feed and product hydrocarbons. This effluent is normally cooled by indirect heat exchange against the stream entering the reaction zone and then further cooled through the use of air or cooling water. The temperature of the effluent stream is normally lowered sufficiently to effect the condensation of substantially all of the feed and product hydrocarbons having six or more carbon atoms per molecule. The resultant mixed-phase stream is passed into a vapor-liquid separator wherein the two phases are separated. The hydrogen-rich vapor is recycled. The condensate is passed into a stripping column in which substantially all $C_5$ and lighter hydrocarbons present in the effluent are concentrated into an overhead stream and removed from the process. The remaining hydrocarbons are removed as a net stripper bottoms stream which is referred to herein as the transalkylation zone effluent stream.

The transalkylation conditions employed in the subject process normally include a temperature of from about 200° C. to about 525° C. The temperature required to maintain the desired degree of conversion will increase as the catalyst gradually loses activity during processing. Normal end-of-run temperatures may therefore exceed start-of-run temperatures of 65 centigrade degrees or more. Preferably, the average temperature is between 350° C. and 500° C. The reaction zone of the transalkylation zone is operated at moderately elevated pressures broadly ranging from about 1.0 to 60 atmospheres gauge. A preferred pressure range is from 20 to 35 atmospheres. The transalkylation reaction can be effected over a wide range of space velocities. A general range of suitable space velocities is from about 0.2 to about 10.0. A preferred range of space velocities is from 0.8 to 3.0. These ranges refer to liquid hourly space velocities.

A large number of solid transalkylation catalysts have been developed. For instance, previously referred to U.S. Pat. No. 3,729,521 describes 27 different catalysts which were tested for transalkylation activity and selectivity. The catalyst providing the best performance was prepared to contain 2.5 wt. % cobalt oxide and 10 wt. % molybdenum trioxide deposited on a support which contained 35 wt. % ultrastable, large-pore crystalline aluminosilicate material suspended in and distributed throughout a matrix of catalytically active alumina. In another embodiment, the ultrastable, large-pore crystalline aluminosilicate material is suspended in an amorphous silica-alumina cracking catalyst. Previously cited U.S. Pat. No. 3,849,340 describes a catalyst useful for the transalkylation of toluene which comprises a zeolite component having a mordenite crystal structure and having a silica to alumina mole ratio of at least 40:1 prepared by acid extracting alumina from an initial mordenite composition having a silica to alumina mole ratio of about 12:1 to 30:1 and a metal component selected from the group consisting of copper, silver, gold and zirconium.

The subject transalkylation process preferably employs a catalyst similar to that described in U.S. Pat. No. 4,083,886. It is characterized by a method of preparation wherein a zeolite having a mordenite crystal structure and a sodium content of less than about 5 wt. % as $Na_2O$ is subjected to an aqueous ammoniacal treatment at a pH of at least about 9.5 and calcined in intimate admixture with a refractory inorganic oxide.

The transalkylation zone effluent stream is passed into a fractionation zone which is referred to as the second fractionation zone or product fractionator in the more limited embodiments of the invention. This fractionation zone may comprise three fractionation columns arranged as shown in the Drawing. A product stream containing $C_{10}$ hydrocarbons, a second product stream containing substantially all of the product $C_8$ alkylaromatic hydrocarbons, and at least one recycle stream are produced in this zone. The necessary recycle stream will contain a mixture of $C_9$ and $C_{10}$ alkylaromatic hydrocarbons and is preferably withdrawn from the last column in the fractionation zone as a liquid sidecut stream. Most of the indane which enters the transalkylation zone as part of the principal transalkylation zone feed stream is converted to other compounds within the transalkylation zone, and the transalkylation zone effluent stream and the $C_9$-plus recycle stream will therefore be essentially free of indane. This allows the recycling of $C_{10}$ hydrocarbons without recycling indane which, due to its small quantity and overlapping boiling point, is difficult to remove completely by fractionation. By recycling the $C_{10}$ alkylaromatic hydrocarbons it is projected that the total yield of $C_8$ alkylaromatic hydrocarbons, and in limited embodiments of the invention paraxylene, will be increased.

A broad embodiment of the invention may therefore be characterized as a transalkylation process which comprises the steps of passing a first feed stream which comprises $C_9$ alkylaromatic hydrocarbons, a first recycle stream which comprises toluene and a second recycle stream which comprises $C_9$ and $C_{10}$ alkylaromatic hydrocarbons into a transalkylation zone maintained at transalkylation conditions and thereby producing a transalkylation zone effluent stream which comprises $C_7$-$C_{10}$ alkylaromatic hydrocarbons; and passing the transalkylation zone effluent stream into a fractionation zone, and withdrawing from the fractionation zone a light hydrocarbon stream which is rich in toluene and is utilized as said first recycle stream, a heavy hydrocarbon stream comprising $C_{10}$ alkylaromatic hydrocarbons and which is rich in $C_9$ alkylaromatic hydrocarbons and is utilized as said second recycle stream, a product stream which is rich in $C_8$ alkylaromatic hydrocarbons and is withdrawn from the process, and a bottoms stream comprising $C_{10}$ alkylaromatic hydrocarbons which is withdrawn from the process with the heavy hydrocarbon stream, the product stream, and the bottoms stream being withdrawn from the same fractionation column.

A more limited embodiment of the subject invention includes a paraxylene separation zone and a xylene isomerization zone to produce a product stream of high purity paraxylene. Referring now to the Drawing, a process feed stream comprising $C_8$ and heavier alkylaromatic hydrocarbons enters the overall process through line 1 and enters a fractionation column 2 of a first fractionation zone. This fractionation column is designed and operated to separate the entering hydrocarbons into a net overhead stream removed in line 25 which comprises substantially all of the $C_8$ aromatics present in the feed stream. The net bottoms stream of the fractionation column 2 is removed in line 3 and contains substantially all of the $C_9$ and heavier aromatic hydrocarbons present in the feed stream. The hydrocarbons flowing through line 3 are passed into a second fractionation column 4 which is designed and operated to separate the entering hydrocarbons into a relatively small stream of $C_{10}$-plus hydrocarbons removed from the process as a net bottoms stream of the fractionation column through line 6 and a net overhead stream containing substantially all of the $C_9$ aromatic hydrocarbons present in the feed stream carried by line 5. Indane which enters the process through line 1 may be rejected to any extent desired in the column bottoms carried by line 6.

The stream of $C_9$ alkylaromatic hydrocarbons carried by line 5 is admixed with an optional stream carried by line 7 which comprises toluene and may also if desired comprise benzene. Assuming benzene is carried by line 7, this admixture would form a stream comprising benzene, toluene and $C_9$ alkylaromatic hydrocarbons carried by line 8 which is then admixed with a recycle stream carried by line 9 which comprises $C_9$ and $C_{10}$ alkylaromatic hydrocarbons. The result of this second admixture is a stream comprising benzene, toluene and $C_9$ and $C_{10}$ aromatic hydrocarbons. This stream is passed into a transalkylation zone 11 through line 10. In the transalkylation zone, the entering hydrocarbons are contacted with a suitable catalyst maintained at transalkylation promoting conditions to effect the production of $C_8$ alkylaromatic hydrocarbons and a net consumption of $C_9$ alkylaromatic hydrocarbons. $C_5$-minus byproduct hydrocarbons are removed from this zone in a line not shown. There is thereby produced a transalkylation zone effluent stream carried by line 12 which comprises benzene and $C_7$-$C_{10}$ alkylaromatic hydrocarbons. The benzene concentration will normally not be large as not much benzene is produced from a $C_9$ feed stream.

The transalkylation zone effluent stream is passed into a second fractionation zone which comprises two or three fractionation columns. If benzene is to be recovered, substantially all of the benzene present in the transalkylation zone effluent stream is separated into a net overhead stream in column 13 and removed from the column in line 14. All or a part of this benzene may be removed from the process as a net product stream through line 15 with the remainder being recycled through line 16. If all of the benzene is to be recycled to the transalkylation zone the benzene and toluene can be removed as a combined overhead stream in a single column such as column 18 thus rendering column 13 unnecessary. When benzene is to be recovered as a product the net bottoms stream of the fractionation column 13 comprises $C_7$-$C_{10}$ alkylaromatic hydrocarbons and possibly a slight amount of heavier hydrocarbons produced in the transalkylation zone. This stream is passed into an intermediate point of a subsequent fractionation column 18 and is divided into a net overhead stream removed through line 19 which comprises toluene and a net bottoms stream removed through line 21 which comprises substantially all of the $C_8$-plus aromatic hydrocarbons which enter this column. The entire net overhead stream of column 18 is preferably recycled to the transalkylation zone through lines 19, 20 and 7.

The $C_8$-plus hydrocarbons carried by line 21 are passed into column 22 which is designed and operated to separate the entering hydrocarbons into a net overhead stream carried by line 23 which comprises substantially all of the entering $C_8$ hydrocarbons and two other streams which contain substantially all of the $C_9$-plus aromatics. These two streams are a sidecut stream removed from the column at a point below the feed point to the column which comprises substantially all of the $C_9$ alkylaromatic hydrocarbons which were originally present in the transalkylation zone effluent stream and which also contains a sizable percentage of the $C_{10}$ aromatics which were present in the transalkylation zone effluent stream. This sidecut stream is recycled to the transalkylation zone through line 9 to increase the production of $C_8$ alkylaromatic hydrocarbons. This stream, referred to herein as the heavy hydrocarbon stream preferably contains between 30 and 70 mole percent of the $C_{10}$ alkylaromatics present in the transalkylation zone effluent stream. A net bottoms stream is removed from column 2 in line 33 and is withdrawn from the process. This net bottoms stream contains some of the $C_{10}$ hydrocarbons present in the transalkylation zone effluent stream and most heavier hydrocarbons which were present in this stream.

The stream of $C_8$ alkylaromatic hydrocarbons carried by line 23 is admixed with the effluent of a xylene isomerization zone carried by line 32 and with the stream of $C_8$ alkylaromatic hydrocarbons carried by line 25. This admixture forms a feed stream carried by line 27 to a paraxylene separation zone 28. The separation zone effects the selective removal of paraxylene from the entering $C_8$ hydrocarbons to produce a product stream of high purity paraxylene removed from the process through line 29. The paraxylene separation zone will also produce a paraxylenedeficient $C_8$ hydrocarbon stream carried by line 30 to the xylene isomerization zone 31. In this zone, the entering $C_8$ hydrocarbons are contacted with an isomerization catalyst maintained at appropriate isomerization-promoting conditions to produce an effluent stream which contains a near equilibrium mixture of the various xylene isomers. This stream is then recycled through lines 32, 26 and 27 to the xylene separation zone to recover additional paraxylene. Any excessive $C_7$-minus hydrocarbons produced in this loop are separated by fractionation in the isomerization zone and removed in a line not shown.

Those skilled in the art will appreciate that the overall flow of the process and especially the flow within the fractionation zone is subject to considerable variation. For instance, as previously described the entire transalkylation zone effluent stream may be passed into a column which produces a net overhead stream containing substantially all of the benzene and toluene present in the effluent stream. It is also possible, although not desired, that the transalkylation zone effluent stream may be fractionated in a reverse order with the heaviest components being first removed as separate streams. For instance, the transalkylation zone effluent stream could be passed into an initial column which produces the small stream of $C_{10}$-plus material and a sidecut stream containing the admixture of $C_9$ and $C_{10}$ aromatics which is recycled and an overhead stream which contains the $C_8$-$C_6$ aromatic hydrocarbons. The overhead stream of this column would then be passed into a subsequent fractionation column for the separation of the $C_8$ hydrocarbons from the remaining $C_6$ and $C_7$ hydrocarbons.

The paraxylene separation zone may use any one of several different separation techniques such as fractionation, crystalization or selective adsorption to remove paraxylene from the stream of mixed xylenes which enters the paraxylene separation zone. The preferred paraxylene separation zone contains a bed of molecular sieves operated in accordance with the teaching of U.S. Pat. No. 3,201,491 to simulate the use of a continuously moving bed of molecular sieves. Subsequent improvements to the process are described in U.S. Pat. Nos. 3,696,107 and 3,626,020. The preferred paraxylene separation zone is therefore operated at adsorption conditions which include temperatures in the range of from 30° to about 300° C., but preferably from 40° to 250° C. This zone may operate with either vapor phase or liquid phase process streams, with liquid phase operations being preferred. Pressures utilized may vary from atmospheric to about 1,000 psig., with more moderate pressures of from about 100 to 300 psig. being preferred. It is preferred that the molecular sieves are contained in one or more vertical columns, with the inlet and outlet positions of the feed stream, raffinate stream, extract stream and desorbent stream being periodically and unidirectionally shifted to simulate a continuous moving bed of the adsorbent. The effluent streams of the adsorbent bed are fractionated as necessary to remove contaminants introduced by these changes in the inlet and outlet locations. The desorbent utilized in the process is recovered during this fractionation and recycled to the bed of adsorbent. This results in a continuous process which produces a xylene product stream containing over 98% paraxylene. A more detailed description of this process is contained in an article entitled "The Parex Process for Recovering Paraxylene" which appeared at page 70 of *Chemical Engineering Progress*, Vol. 66, No. 9, September, 1970. Further details on the operation of the preferred paraxylene separation zone may also be obtained from U.S. Pat. Nos. 4,039,599 and 4,184,943. The paraxylene separation zone may depart from this preferred mode of operation through the use of batch-type operations or a true moving bed of solid adsorbent.

As used herein, the term "molecular sieves" is intended to refer to various natural and synthetic aluminosilicate adsorbents which exhibit an ability to preferentially adsorb selected xylene isomers. Preferred for use in the separation zone are synthetically prepared type X and type Y zeolites containing selected cations at the exchangeable cationic sites within the crystal structure. One suitable molecular sieve is a cation exchanged type X or type Y zeolite containing a single cation selected from potassium, barium, sodium and silver. A second suitable molecular sieve is a type X or type Y zeolite containing both a first cation chosen from the group consisting of potassium, rubidium, cesium, barium and silver, and a second cation selected from the group consisting of lithium, sodium, magnesium, calcium, strontium, beryllium, cadmium, cobalt, nickel, copper, manganese and zinc. These molecular sieves are described in greater detail in U.S. Pat. No. 3,626,020. Other adsorbents, including those not yet developed, could be used if they meet the criteria of adequate selectivity and longevity necessary for commercial operation. Two other adsorbents which are suitable for paraxylene separation are described in U.S. Pat. Nos. 3,943,183 and 3,943,184.

The two major effluent streams of the paraxylene separation zone are the paraxylene product stream and a raffinate stream which contains the remaining orthoxylene and metoxylene and which is passed into a xylene isomerization zone. This isomerization zone may be of any type or configuration which is capable of effecting the catalytic isomerization of orthoxylene and metaxylene, and ethylbenzene if it is present, into paraxylene at commercially acceptable rates and conditions. Moving bed reactors, fixed bed reactors and fluidized reactors may all be used to perform the isomerization reaction. These reactors are subject to further variation in that the hydrocarbon reactants may be passed through the catalyst as a vapor or as a liquid, and in that the reactor may be operated with upward, downward or radial reactant flow.

The isomerization zone is operated at conditions effective to cause the isomerization of ortho- and metaxylene to paraxylene. Besides the presence of a catalyst, these conditions include a temperature of about 0° C., to about 600° C., and preferably 320° C. to about 450° C., and a pressure of from about 1.0 to 100 atmospheres. Preferred is a pressure in the range of about 7 to 28 atmospheres and the use of a single fixed bed reactor operated with a downward flow of vapor phase reactants. Hydrogen should be circulated through the reactor at a rate sufficient to maintain a hydrogen to hydrocarbon mole ratio of from 1:1 to about 20:1 in the reactor. This ratio is preferably kept within the range of about 1.5:1 to about 8:1. The quantity of catalyst within the reactor should provide a weight hourly space velocity (weight of hydrocarbons passing through the reactor in 1 hour per unit weight of catalyst) of about 0.5 to about 10 and preferably about 1 to 5. The exact conditions employed will normally vary with the age and usage of a catalyst and are set by the activity of the catalyst and the effect of the conditions on selectivity, conversion and ultimate xylene yield of the isomerization zone.

Central to the operation of the xylene isomerization zone is an effective isomerization catalyst. Several different suitable formulations are known to those skilled in the art and effective catalysts are available commercially. The catalyst will typically comprise an acidic inorganic oxide support such as alumina, silica-alumina mixtures, faujasites and mordenites which have been combined or impregnated with a metallic component. Preferred is an alumina-based catalyst containing about 0.05 to about 5.0 wt. % of a Group VII metallic component and 0.3 to 5.0 wt. % of platinum or palladium and about 0.5 to 2.5 wt. % fluorine or about 0.1 to 1.5 wt. % chlorine. This halogen concentration may be maintained by the injection of halogen-containing substances such as carbon tetrachloride into the material entering the isomerization zone. These catalytic composites may in addition contain from about 0.1 to about 1.0 wt. % sulfur to improve their performance. All percentages given in reference to catalyst composition are calculated on an elemental basis. Other catalysts which may be employed in the xylene isomerization zone are described in some detail in U.S. Pat. Nos. 3,464,929; 3,409,685 and 3,409,686.

A significant amount of hydrocarbons containing 7 or fewer carbon atoms per molecule will be produced within the xylene isomerization zone reactor. Therefore, after an initial partial condensation and phase separation performed to facilitate the recycling of hydrogen, the remainder of the effluent of the isomerization reactor is passed into a first fractionation column which is operated as a stripping column, normally a deheptanizer. Some recycling of toluene in the isomerization zone is preferred. The excess toluene which is produced in the isomerization zone is removed as part of the deheptanizer overhead and may be recovered for passage into the transalkylation zone. The bottoms stream of the deheptanizer is passed into a second fractionation column which splits the entering aromatic hydrocarbons into a net overhead stream comprising all of the entering hydrocarbons except for a small amount of C$_9$-plus material which is removed as a net bottoms stream. The overhead stream of this fractionation column is recycled to the paraxylene separation zone for the recovery of the paraxylene produced in the isomerization zone, and the net bottoms stream of this column may be withdrawn from the process, passed into the first fractionation zone located upstream of the transalkylation zone, or passed directly into the transalkylation zone through a line not shown on the Drawing. If it is desired to simultaneously produce orthoxylene, then the desired amount of orthoxylene is removed as part of the bottoms product of the second fractionation column, and this bottoms stream is then passed into a third fractionation column referred to as an orthoxylene rerun column. The orthoxylene is then recovered as the overhead stream of this rerun column, and the net bottoms stream may be treated as just described. The fractionation of the xylene reactor effluent is described in U.S. Pat. Nos. 3,856,871; 3,856,872; 3,856,873; 3,856,874; 3,939,221 and 4,039,599. As the process of the subject invention is not directly effected by the manner in which the xylene isomerization zone reactor effluent is fractionated, the required fractionation facilities have not been shown in the Drawing and are to be considered as being part of the xylene isomerization zone.

A limited embodiment of the invention may be characterized as a process for the production of paraxylene which comprises the steps of separating a feed stream which comprises a mixture of C$_8$, C$_9$ and C$_{10}$ alkylaromatic hydrocarbons in a first fractionation zone into a first C$_8$ stream which is rich in C$_8$ alkylaromatic hydrocarbons, a first C$_9$ stream which is rich in C$_9$ alkylaromatic hydrocarbons, and a first bottoms stream which is rich in C$_{10}$ alkylaromatic hydrocarbons; passing the first C$_9$ stream, a first recycle stream which comprises toluene, and a second recycle stream which comprises C$_9$ and C$_{10}$ alkylaromatic hydrocarbons into a transalkylation zone maintained at transalkylation conditions and thereby producing a transalkylation zone effluent stream which comprises C$_7$–C$_{10}$ alkylaromatic hydrocarbons; separating the transalkylation zone effluent stream in a second fractionation zone and thereby producing a light hydrocarbon stream which is rich in toluene and is utilized as said first recycle stream, a heavy hydrocarbon stream comprising C$_{10}$ alkylaromatic hydrocarbons which is rich in C$_9$ alkylaromatic hydrocarbons and is utilized as said second recycle stream, a second C$_8$ stream which is rich in C$_8$ alkylaromatic hydrocarbons, and a second bottoms stream which is rich in C$_{10}$ alkylaromatic hydrocarbons, with the heavy hydrocarbon stream, the second C$_8$ stream and the second bottoms stream being withdrawn from the same column; and passing the first C$_8$ stream, the second C$_8$ stream and a third recycle stream into a paraxylene separation zone in which paraxylene is concentrated into a paraxylene-rich product stream which is removed from the process and thereby producing a paraxylene separation zone effluent stream comprising metaxylene; and, passing the paraxylene separation zone effluent stream into a xylene isomerization zone and thereby producing an isomerization zone effluent stream comprising paraxylene, orthoxylene and metaxylene which is utilized as said third recycle stream. This embodiment may include the passage of separate streams, or a combined stream, of toluene and C$_9$-plus alkylaromatics from the isomerization zone to the transalkylation zone or to the upstream first fractionation zone.

I claim as my invention:

1. A transalkylation and isomerization process for the production and recovery of p-xylene which comprises the steps of:
   (a) separating a feed stream comprising indane, C$_8$, C$_9$ and C$_{10}$ alkylaromatic hydrocarbons, in a first fractionation zone comprising two fractionation columns into a first C$_8$ stream rich in C$_8$ alkylaromatic hydrocarbons and which stream contains less than 5 mole percent C$_9$+ hydrocarbons, a first C$_9$ stream rich in C$_9$ alkylaromatic hydrocarbons and a first bottoms stream rich in C$_{10}$ alkylaromatic hydrocarbons and which stream contains at least 50 mole percent of said indane in said feed stream;
   (b) passing said first C$_9$ stream, a first recycle stream rich in toluene and a second recycle stream comprising C$_9$ and C$_{10}$ alkylaromatic hydrocarbons into a transalkylation zone maintained at transalkylation conditions to produce a transalkylation zone effluent stream comprising C$_7$ to C$_{10}$ alkylaromatic hydrocarbons;
   (c) separating said transalkylation zone effluent stream in a second fractionation zone to produce a light aromatic hydrocarbon stream rich in toluene and which is used as said first recycle stream, a heavy hydrocarbon stream comprising C$_{10}$ alkylaromatics and which is rich in C$_9$ alkylaromatic hydrocarbons and which is used as said second recycle stream, a second C$_8$ stream rich in C$_8$ alkylaromatic hydrocarbon and a second bottoms stream rich in C$_{10}$ alkylaromatic hydrocarbon and which is removed from said process;
   (d) combining said first and second C$_8$ streams with a hereinafter defined third recycle stream;
   (e) passing said combined streams of (d) into a paraxylene separation zone wherein paraxylene is concentrated in a paraxylene-rich product stream, which is recovered as the product stream of said process, and a paraxylene separate zone effluent stream is produced comprising metaxylene;
   (f) passing said paraxylene separate zone effluent stream comprising metaxylene into a xylene isomerization zone to isomerize said effluent to produce an isomerization zone effluent stream comprising paraxylene, orthoxylene and metaxylene; and
   (g) recycling at least a portion of said isomerization zone effluent stream to said paraxylene separation zone as said third recycle stream of step (d).

2. The process of claim 1 further characterized in that the transalkylation zone effluent stream and the light hydrocarbon stream comprise benzene.

3. The process of claim 2 further characterized in that between 30 and 70 mole percent of the C$_{10}$ alkylaromatic hydrocarbons present in the transalkylation zone effluent stream are concentrated into the heavy hydrocarbon stream within the second fractionation zone.

4. The process of claim 3 further characterized in that at least 40 mole percent of the C$_{10}$ alkylaromatic hydrocarbons present in the transalkylation zone effluent stream is concentrated into the heavy hydrocarbon stream within the second fractionation zone.

5. The process of claim 4 further characterized in that the heavy hydrocarbon stream is withdrawn from a fractionation column in the second fractionation zone as a sidecut stream at an intermediate point below the feed point of the fractionation column.

6. The process of claim 3 further characterized in that substantially all of the benzene present in the transalkylation zone effluent stream is concentrated into the light hydrocarbon stream within the second fractionation zone.

7. The process of claim 6 further characterized in that a bed of solid adsorbent which selectively adsorbs paraxylene is utilized within the paraxylene separation zone.

8. The process of claim 1 further characterized in that a stream comprising toluene is removed from the xylene isomerization zone and passed into the transalkylation zone.

9. The process of claim 8 further characterized in that $C_9$-plus alkylaromatic hydrocarbons are withdrawn from the xylene isomerization zone and passed into the transalkylation zone.

* * * * *